(12) United States Patent
O'Brien et al.

(10) Patent No.: US 11,648,401 B2
(45) Date of Patent: May 16, 2023

(54) SYSTEMS AND METHODS FOR PLACEMENT OF SPINAL CORD STIMULATOR LEADS

(71) Applicant: SafeOp Surgical, Inc., Hunt Valley, MD (US)

(72) Inventors: Richard O'Brien, Hunt Valley, MD (US); Robert Snow, Hunt Valley, MD (US)

(73) Assignee: SafeOp Surgical, Inc., Carlsbad, CA (US)

( * ) Notice: Subject to any disclaimer, the term of this patent is extended or adjusted under 35 U.S.C. 154(b) by 135 days.

(21) Appl. No.: 16/348,437

(22) PCT Filed: Nov. 13, 2017

(86) PCT No.: PCT/US2017/061410
§ 371 (c)(1),
(2) Date: May 8, 2019

(87) PCT Pub. No.: WO2018/089950
PCT Pub. Date: May 17, 2018

(65) Prior Publication Data
US 2019/0275333 A1    Sep. 12, 2019

Related U.S. Application Data

(60) Provisional application No. 62/421,797, filed on Nov. 14, 2016.

(51) Int. Cl.
*A61N 1/36* (2006.01)
*A61B 5/00* (2006.01)
(Continued)

(52) U.S. Cl.
CPC ............ *A61N 1/36139* (2013.01); *A61B 5/24* (2021.01); *A61B 5/316* (2021.01); *A61B 5/389* (2021.01);
(Continued)

(58) Field of Classification Search
CPC ............ A61N 1/36017; A61N 1/36021; A61N 1/0553; A61N 1/36003; A61N 1/36071;
(Continued)

(56) References Cited

U.S. PATENT DOCUMENTS

| 4,026,301 | A | | 5/1977 | Friedman et al. |
| 6,027,456 | A | * | 2/2000 | Feler ................... A61N 1/36021 600/554 |

(Continued)

FOREIGN PATENT DOCUMENTS

| CN | 105744887 A | 7/2016 |
| CN | 105769169 A | 7/2016 |

(Continued)

*Primary Examiner* — Jon Eric C Morales
(74) *Attorney, Agent, or Firm* — Mintz, Levin, Cohn, Ferris, Glovsky and Popeo, P.C.

(57) ABSTRACT

A method of optimally placing spinal cord stimulator (SCS) leads includes acquiring components of somatosensory evoked potentials (SSEPs), compound action potentials and triggered EMG; analyzing the waveforms; and quantifying waveform features in a single display such that a surgeon can quickly and easily determine optimal placement (as it relates to laterality and level of placement on the spinal cord) of SCS leads in a patient under general anesthesia without additional expert help.

23 Claims, 2 Drawing Sheets

(51) Int. Cl.
*A61N 1/05* (2006.01)
*A61B 5/24* (2021.01)
*A61B 5/316* (2021.01)
*A61B 5/389* (2021.01)

(52) U.S. Cl.
CPC ............ *A61B 5/4893* (2013.01); *A61B 5/743* (2013.01); *A61B 5/746* (2013.01); *A61N 1/0551* (2013.01); *A61N 1/3615* (2013.01); *A61N 1/36062* (2017.08)

(58) Field of Classification Search
CPC ............ A61N 1/36057; A61B 17/1671; A61B 17/1757; A61B 5/389; A61B 5/4893; A61B 8/463
See application file for complete search history.

(56) References Cited

U.S. PATENT DOCUMENTS

| | | |
|---|---|---|
| 2006/0276720 A1 | 12/2006 | McGinnis |
| 2011/0245708 A1 | 10/2011 | Finkel et al. |
| 2012/0014580 A1 | 1/2012 | Blum |
| 2012/0095360 A1 | 4/2012 | Runney |
| 2014/0051999 A1* | 2/2014 | Gharib ................ A61B 5/4893 |
| | | 600/439 |
| 2014/0296737 A1 | 10/2014 | Parker |
| 2014/0330340 A1* | 11/2014 | Bennett .............. A61N 1/36057 |
| | | 607/46 |

FOREIGN PATENT DOCUMENTS

| | | |
|---|---|---|
| JP | 2012505707 A | 3/2012 |
| JP | 2013523274 A | 6/2013 |
| JP | 5830090 B2 | 12/2015 |
| WO | WO 0002623 A1 | 1/2000 |
| WO | 2005007029 A2 | 1/2005 |
| WO | 2010044880 A1 | 4/2010 |
| WO | WO 2016090420 A | 6/2016 |
| WO | 2018089950 A1 | 5/2018 |

* cited by examiner

SYSTEMS AND METHODS FOR PLACEMENT OF SPINAL CORD STIMULATOR LEADS

CROSS REFERENCE TO RELATED APPLICATIONS

This application claims priority to International Application No. PCTUS2017/061410, filed on Nov. 13, 2017, which claims the priority to U.S. Provisional Application No. 62/421,797 filed Nov. 15, 2016, each of which is incorporated herein by reference in its entirety.

BACKGROUND

The present invention relates generally to a medical device to facilitate positioning of spinal cord stimulator lead, and in particular a medical device to enable the accurate placement of spinal cord stimulator leads and easily display that information to the user without use of intraoperative conscious patient feedback.

Application of electrical stimulating pulses to spinal nerve roots, spinal cord, and other nerve and bundles for the purpose of chronic pain control has been actively practiced since the 1960s. Applying electrical pulses to areas of the spinal cord associated with the regions of the body afflicted with chronic pain can induce relief, either by producing masking paresthesia or by other means.

While the exact mechanism by which the pain relief is induced remains unclear, critical to the efficacy of these spinal cord stimulator (SCS) devices is the accurate placement of the stimulating electrode at or near the area of the spinal cord, dorsal root ganglia or peripheral nerve transmitting the painful stimuli. Correct positioning requires placement of stimulating electrode or electrode array such that it produces an electrical field in the desired location, both relative to a physiological midline and longitudinally along the spinal cord relative to the pain source or transmitting neural structures. Stimulating electrodes are typically positioned external to the dural layer (extra-dural) surrounding a spinal cord near the dorsal column (DC) or dorsal root ganglia (DRG) which contain the cell bodies of the sensory neurons. The electrodes are typically inserted by either percutaneous catheter or during laminotomy.

While percutaneous catheters, or percutaneous leads, are commonly placed under a local or spinal anesthetic with the patient sedated but awake, laminotomy leads are placed under general anesthesia (patient unconscious) and require tissue resection but may be favored as they tend to provide increased stability or less likelihood of migration once implanted. They also arguably provide finer control over where the electrode is placed.

Final determination of what tissue the SCS electrode is effecting may depend upon questioning a sedated patient for percutaneous insertion, or radiological evaluation for the patient receiving spinal or general anesthesia. In the latter case, while awakening a patient during a trial insertion is possible, it subjects the patient to increased discomfort and provides feedback confounded by their sedation.

Incorrect placement of the electrode can result in insufficient or no pain relief and require an additional procedure to fix placement, which leads to further discomfort, possibility of complication and additional cost.

While some devices and methods have been proposed to help in localization of the stimulating electrodes during surgery, they suffer from complicated setup, are cost prohibitive, require availability of expert personnel or have limited usefulness.

Some current techniques relating to SCS and the measurement of electro-physiological signals involve the use of one or more of several techniques including somatosensory evoked potentials (SSEP), motor evoked potentials (MEP), sensory nerve action potentials (SNAP), electromyography (EMG) or triggered electromyography and compound motor action potentials (T-EMG and CMAP).

SSEPs are summated electrical potentials that are generally elicited by stimulating peripheral nerves or a sensory pathway and recording the resulting waveforms as they travel to the brain. Motor evoked potentials are recordings from muscle after stimulation of the brain, usually using a brief series of linked stimuli. Sensory nerve action potentials are measured by stimulating a nerve with sensory fibers and recording the depolarization wave over the same nerve at a distance from the stimulation site. Compound action potentials are direct nerve recordings from an evoked stimulus on the same nerve. Triggered EMG is the response of a muscle when its motor nerve is stimulated.

U.S. Pat. No. 6,027,456 entitled "Apparatus and Method for Positioning Spinal Cord Stimulation Leads" to Feler et al describes a device for aiding in spinal cord stimulator implantation, however this device and method require the ability to connect to the SCS electrode directly and record resultant somatosensory evoked potentials or sensory nerve action potentials from the level of SCS stimulation, which is technically difficult, may require adapters for attaching to differing spinal stimulator connectors, and measures only the production of sensory impulses, and does not measure the degree of interference with transmission of sensory potentials at the site of placement.

Other current methods depend upon determining the interruption of transmission of sensory impulses by SCS electrical stimulations through the DC pathways of the spinal cord as they pass over the SCS placement site. Since pathways exist for both the right and left sensory fibers that can be measured independently, laterality of the interfering SCS stimulation activity can be determined by its degree of or relative degree of interference on each side. Laterality of placement can also be determined by induction of and measurement of muscle activity via electromyograms (EMG) induced by the SCS stimuli on the adjoining spinal cord motor nerve component as opposite sides of the body are served by nerves that exit at a distance from each other on either side of the spinal cord. The presence of activity in these muscles also serves to allow determination of the level of the placement of the SCS on the spinal cord. These techniques require measurement of somatosensory evoked potentials (SSEP) measured at the cortical level and either CMAPO, T-EMG or SNAP techniques.

These techniques are not automated, do not have a uniform display technology, do not have a standardized method of measuring significant changes, require expensive multi-modality equipment and specialized personnel and expertise and are simply not practical or cost effective for a short SCS placement surgery. In addition, they do not measure interruption of the pain pathway stimuli, only those of the pathways transmitting light touch and vibration sensation at the same level.

US Publication No. 2016/0213314 to Zuckerman-Stark describes a method of objectively determining the effectiveness of SCS treatment using physiological measurements, but only after implantation has occurred. In addition, since it is the subjective relief of pain that is the goal, usefulness may be limited.

SUMMARY

The present disclosure relates to an automated device and method to enable an implanting physician to accurately and quickly position one or more spinal cord stimulating leads while minimizing the operative discomfort of the patient that overcomes some or all of the aforementioned shortcomings of current methods and systems.

In one embodiment, there is a method of optimally placing spinal cord stimulator (SCS) leads and, more particularly, an apparatus and method for acquiring several components of somatosensory evoked potentials (SSEPs), compound action potentials and triggered EMG, analyzing those waveforms using proprietary algorithms and quantifying waveform features in a single display such that a surgeon can quickly and easily determine optimal placement (as it relates to laterality and level of placement on the spinal cord) of SCS leads in a patient under general anesthesia without additional expert help.

In some embodiments, the method may include stimulating one or more peripheral nerves with one or more electrical pulses from one or more stimulating electrodes; recording resultant electrical waveforms generated by a nervous system of the patient in response to the electrical pulses using one or more recording electrodes; and identifying, by or with one or more computing devices, the position of the spinal cord stimulator based on the resultant electrical waveforms or interference with the resultant electrical waveforms caused by activation of the SCS.

In some embodiments, the one or more stimulating electrodes may be coupled to one or more of an arm of the patient, a leg of the patient, an ulnar nerve of the patient, a median nerve of the patient, or a posterior tibial nerve of the patient. In some embodiments, the one or more recording electrodes may be coupled to one or more of a head of the patient or a neck of the patient or over muscles served by spinal nerves adjacent to the desired placement level of the SCS, including the $7^{th}$, $8^{th}$ and $9^{th}$ Thoracic levels and the $2^{nd}$ to $8^{th}$ Cervical levels.

In some embodiments, the resultant electrical waveforms may be somatosensory evoked potential waveforms or compound motor action potentials or electromyographic potentials.

In some embodiments, the identifying may include one or more of comparing, with the computing device, information based on the resultant electrical wave forms to information from an SCS machine to determine when changes in the resultant electrical waveforms are due to SCS stimulating activity and/or comparing, with the one or more computing devices, information based on the resultant electrical waveforms to a baseline level of activity for each other to determine when changes in the resultant electrical waveforms are due to positioning of the SCS.

In some embodiments, the method may further include providing information based on the intensity of stimulation from an SCS. In some embodiments, the method may further include alerting a user to the positioning of the SCS using one or more of a notification, an alert, a communication, an indication, and/or an alarm. The method may further include displaying information based on the resultant electrical waveforms on a display unit.

In some embodiments, the method may further include receiving a user input regarding the accuracy of the resultant electrical waveforms. In some embodiments, an automated apparatus for detecting lead positioning may include an output operable to connect and/or couple to one or more stimulating electrodes of the SCS to activate them or deactivate them and vary their intensity.

In some embodiments, the processor may further include means for identifying the position of the SCS electrode which may include one or more means for identifying changes in a latency of the resultant electrical waveforms, means for identifying changes in an amplitude of the resultant electrical waveforms, and/or means for identifying changes in a morphology of the resultant electrical waveforms.

In some embodiments, the apparatus may further include a display unit, connected and/or coupled to the one or more processors, operable to display information regarding the resultant electrical waveforms. In some embodiments, the apparatus may further include an alert unit, coupled to the one or more processors, operable to alert a user to the position of the SCS electrode. In some embodiments, the apparatus may further include an interface, connected and/or coupled to the processor, operable to couple a table to the processor. In some embodiments, the apparatus may further include a unified display that depicts various waveforms signals being collected as well as a pictogram indicating the computed likely position of the SCS stimulator electrode based on those inputs.

Further features and advantages of the invention, as well as the structure and operation of various exemplary embodiments of the invention, are described in detail below with reference to the accompanying drawings.

DETAILED DESCRIPTION

Various exemplary embodiments of the invention including preferred embodiments are discussed in detail below. While specific exemplary embodiments are discussed, it should be understood that this is done for illustration purposes only. A person skilled in the relevant art will recognize that other components and configurations can be used without parting from the spirit and scope of the invention.

Spinal cord stimulators are devices that deliver pulsed electrical energy near the spinal cord, usually on its dorsal surface and just outside the tough protective dural membrane (in the epi-dural space). The purpose of the stimulators is to modulate pain impulses and reduce painful sensations in patients with chronic pain syndromes such as those associated with 'failed back syndrome' after failed spinal surgery. The devices in general consist of two parts: a pulse generator placed at a distance from the spinal cord and an electrode lead/electrode that carries the impulses to the desired spinal cord area.

For these stimulators to be effective, the spinal cord stimulator lead/electrode must be placed at the desired spinal cord level and in the appropriate medial-lateral position (midline or to the side) along the spinal cord so that the impulses can affect the desired spinal tracts, nerves and levels that are carrying the unwanted painful stimuli. Since the spinal cord is much shorter than the boney spinal column in which it lies, the boney spinal column level cannot be relied upon to determine that the spinal cord lead is at the effective or desired spinal cord level. In addition, it is difficult to determine if the placement of a lead is in the midline or off to one side.

A more effective method of determining if the SCS lead is in the correct position is to measure its physiological effect on the spinal cord and spinal nerves, allowing precise placement in relation to the actual painful impulse. Unfortunately, the easiest way of doing this is to wake the patient during a procedure and ask them what the effects are of turning on a SCS device. This is not always possible or even desired and may lead to complications during the lead placement.

Figure 1:
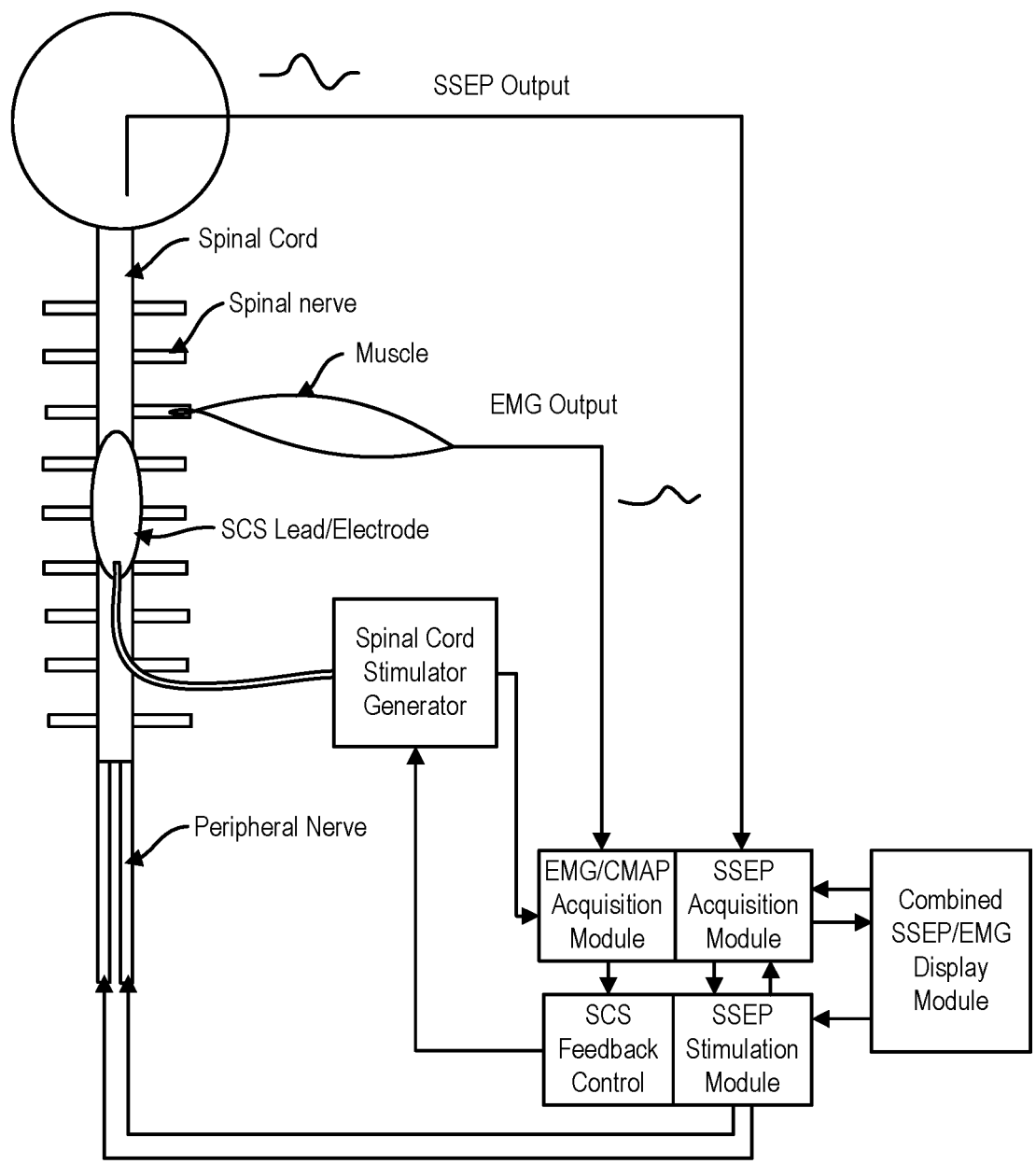
FIG. 1 depicts the flow of inputs and outputs for the device according to an exemplary embodiment.

FIG. 1 depicts a system to assist with proper positioning of a SCS lead by identifying the location of the SCS lead. The system includes a SCS generator 102 that provides electrical stimulation to the spinal cord through one or more SCS electrodes 104. The system further includes an SSEP stimulator for providing electrical stimulation bilaterally through one or more stimulating electrodes to peripheral nerves 106. The one or more stimulating electrodes may be coupled to one or more of an arm of the patient, a leg of the patient, an ulnar nerve of the patient, a median nerve of the patient, or a posterior tibial nerve of the patient. These stimulation pulses produce bilateral SSEP responses that are recorded from one or more recording electrodes 108 at the head or neck. In some embodiments, the one or more recording electrodes may be coupled to one or more of a head of the patient or a neck of the patient. The SSEP responses include components representing transmission over vibration and light touch conduction fibers from lower intensity stimulation, as well as components representing transmission over painful stimuli conducting fibers from higher intensity stimulation.

Identifying the position of the spinal cord stimulator may include comparing information based on the SSEP responses to information from an SCS machine to determine when changes in the resultant electrical waveforms are due to SCS stimulating activity. Alternatively, or in addition to, identifying the positions of the SCS may also include comparing information based on the resultant electrical waveforms to a baseline level of activity for each other to determine when changes in the resultant electrical waveforms are due to positioning of the SCS.

In particular, the device is configured to qualify the SSEP responses automatically using an algorithm, and then automatically measure the changes in those responses after stimuli are applied to the dorsal columns by a spinal cord stimulator. The changes may be measured both relative to baseline and relative to previous responses. For example, the device may allow for identifying changes in a latency of the resultant electrical waveforms, for identifying changes in an amplitude of the resultant electrical waveforms, and/or for identifying changes in a morphology of the resultant electrical waveforms. An algorithm for qualifying and measuring SSEP responses relative to a baseline and to previous responses is described in PCT application number PCT/US2016/030605 entitled "System, Method, and Computer Algorithm for Measuring, Displaying, and Accurately Detecting Changes in Electrophysiological Evoked Potentials" filed May 3, 2016, which is hereby incorporated by reference herein in its entirety.

The resultant information obtained from changes in the SSEP responses when the SCS stimulation is activated indicates the position of the spinal cord stimulator lead in relation to the functional midline which separates the left and right dorsal column sensory tracts. More specifically, a decrease or complete reduction of the left, right or both sided SSEP response indicates the lateral placement of the SCS stimulation. For example, if a recording waveform representative of the SSEP response on the left side records a decrease in SSEP response, it can be concluded that the SCS stimulation is in the proper lateral placement to effectively affect nerve pathways on the left side. If a recording representative of the SSEP response on the right side records a decrease in SSEP response, it can be concluded that the SCS stimulation is in the proper lateral placement to effectively affect the nerve pathways on the right side. If recordings on both sides are equally affected, then it can be concluded that the SCS stimulation is midline relative to the functional behavior of the nerve pathways.

In addition to the detection of the presence and changes in the SSEP potentials, the method and system also includes one or more of electrodes 110 applied to the muscles supplied by the nerve roots of the spinal levels that are targeted for SCS electrode placement or nearby those levels. The electrodes 110 may be positioned over muscles served by spinal nerves adjacent to the desired placement level of the SCS, including the $7^{th}$, $8^{th}$ and $9^{th}$ Thoracic levels and the $2^{nd}$ to $8^{th}$ Cervical levels. Activation of the SCS electrode 104, if it is at the appropriate level, activates the associated nerve roots and their attached muscles (EMG activity) which is detected by the electrode(s) 110. The resultant information showing EMG activity and the location thereof indicates the relative position of the spinal cord stimulator lead in relation to the midline which separates the left and right spinal nerves. The resultant information also indicates the relative position of the spinal cord stimulator lead along the length of the spinal cord, by indicating the location of spinal nerve roots in which the array of electrodes detect an associated muscle response.

In addition, the method and system allows feedback to the SCS pulse generator 102 so that the intensity of the SCS pulses can be varied, allowing detection of the minimum intensity required to produce significant changes in SSEP waveforms and EMG activity, providing additional information on the relative placement of the SCS electrode.

In addition, the method and system may further include providing information based on the intensity of stimulation from an SCS. In some embodiments, the method may further include alerting a user to the positioning of the SCS using one or more of a notification, an alert, a communication, an indication, and/or an alarm. Furthermore, input from a spinal cord stimulator may be received, regarding its level of activity so that it can be correlated with other inputs via direct, wireless, Bluetooth, or other forms of communication.

Figure 2:
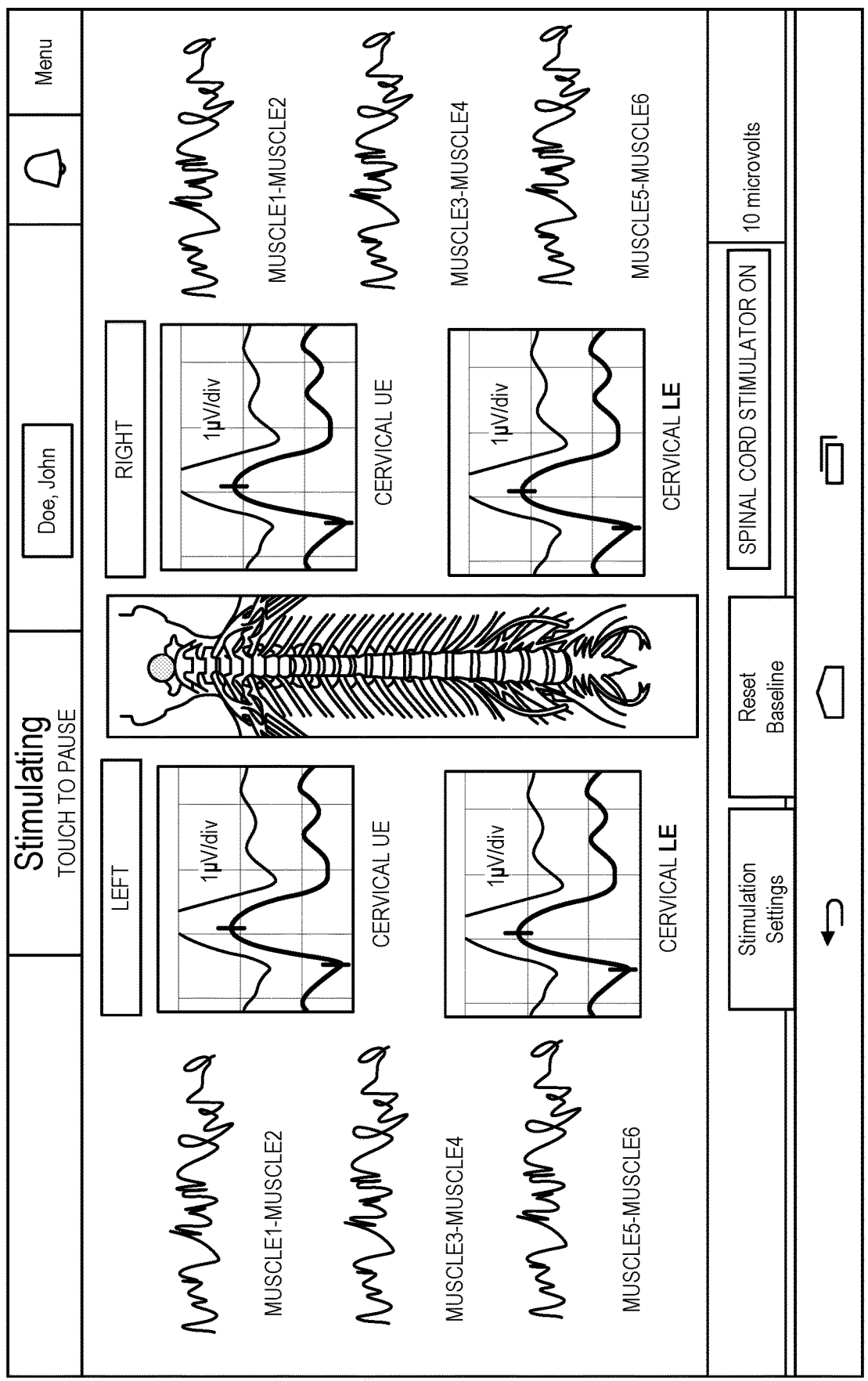
FIG. 2 depicts a display device according to an exemplary embodiment showing various waveforms signals being collected and a pictogram indicating the computed likely position of the SCS stimulator electrode based on the collected signals.

The method and system may further include displaying information based on the resultant electrical waveforms on a display unit in real time as the SCS lead is inserted or moved. All the information described above may be displayed both as processed waveforms and as a pictogram indicating the likely position of the SCS electrode in relation to the spinal cord midline and spinal nerves. An exemplary embodiment of a unified display is depicted in FIG. 2, which shows a display of the dorsal spine with colored markers indicating SSEP laterality of pain pathway block (green) and EMG laterality and level of spinal segment activity (yellow). This single display allows a surgeon or other operating personnel to quickly and easily determine optimal placement (as it relates to laterality and level of placement on the spinal cord) of SCS leads in a patient under general anesthesia without additional expert help and without waking the patient.

What is claimed is:

1. A method for detecting and displaying the position of a spinal cord stimulating lead comprising:
   stimulating one or more peripheral nerve structures with one or more electrical pulses from a stimulating electrode with one or more intensities;
   detecting somatosensory evoked potential responses (SSEPs) to the stimulation of the one or more peripheral nerve structures at the stimulating electrode;
   automatically analyzing the resultant somatosensory evoked potential responses and their components;
   detecting electromyographic responses to stimuli applied by a spinal cord stimulator (SCS) device;
   identifying associated nerve or nerve root level of the electromyographic responses;
   automatically analyzing the electromyographic responses;
   automatically providing information to the SCS device to allow it to adjust the spinal cord stimulator stimulus intensity;
   detecting a lowest level stimulus intensity that produces somatosensory evoked potential conduction block;
   detecting the lowest level of stimulus intensity that produces the initial electromyographic responses on one side or more;
   forwarding data to a display, the data comprising information for displaying an anatomical diagram that depicts a location or side of the detected change in somatosensory evoked potential conduction block or electromyography activation;
   displaying the anatomical diagram on a screen;
   displaying the activity and degree of stimulation of the SCS device relation to the other inputs on the screen;
   calculating the laterality and level of SCS electrode placement;
   locating the laterality and level of SCS electrode placement on a graphic; and
   displaying the calculation and location of the laterality and level of activity on the screen.

2. The method of claim 1, wherein SSEPs comprise a first component representing transmission over vibration and light touch conduction fibers from lower intensity stimulation and a second component representing transmission over painful stimuli conducting fibers from higher intensity stimulation.

3. The method of claim 1, further comprising alerting the user to changes in recorded somatosensory evoked potentials and/or electromyography recordings.

4. The method of claim 1, further comprising receiving input from a spinal cord stimulator regarding its level of activity so that it can be correlated with other inputs via direct, Bluetooth or other forms of communication.

5. A system for detecting the position of a spinal cord stimulation lead, the system comprising:
   a spinal cord stimulation (SCS) generator;
   the spinal cord stimulation lead for providing stimuli from the SCS generator to a spinal cord of a patient;
   an array of electromyographic electrodes for detecting muscle activity responsive to stimuli from the SCS generator;
   a second stimulation generator for stimulating a peripheral nerve structure of the patient with an electrical pulse from a stimulating electrode;
   a detecting electrode for detecting somatosensory evoked potential responses (SSEPs) to the stimulation at the stimulating electrode;
   a computing system comprising a processor, wherein the processor is configured to execute instructions stored in a non-transitory computer-readable medium, which instructions cause the processor to automatically analyze the resultant SSEPs and the detected muscle activity to identify the lateral positioning and level of the SCS lead; and
   a display device for displaying information related to the positioning and level of the SCS lead.

6. The system of claim 5, wherein the processor is configured to:
   instruct the second stimulation generator to stimulate one or more peripheral nerve structures with one or more electrical pulses from the stimulating electrode with one or more intensities;
   detect somatosensory evoked potential responses (SSEPs) to the stimulation at the stimulating electrode;
   automatically analyze the resultant SSEPs and their components;
   detect electromyographic responses to stimuli applied by the SCS generator;
   identify associated nerve or nerve root level of the electromyographic responses;
   automatically analyze the electromyographic responses;
   automatically provide information to the SCS generator to allow it to adjust the spinal cord stimulator stimulus intensity;
   detect the lowest level stimulus intensity that produces somatosensory evoked potential conduction block;
   detect the lowest level of stimulus intensity that produces the initial electromyographic responses on one side or more;
   forward data to the display, the data comprising information for displaying an anatomical diagram that depicts a location or side of the detected change in somatosensory evoked potential conduction block or electromyography activation, the display configured to show an anatomical diagram and to display the activity and degree of stimulation of the spinal cord stimulator in relation to the other inputs on the display;
   calculate the laterality and level of SCS electrode placement;
   locate the laterality and level of SCS electrode placement on a graphic; and
   display the calculation and location of the laterality and level of activity on the display.

7. The system of claim 5, wherein the display device is configured to display information regarding the resultant electrical waveforms.

8. The system of claim 5, further comprising an alert unit, coupled to the processor, operable to alert a user to the position of the SCS electrode.

9. The system of claim 5, further comprising an interface coupled to the processor, operable to couple a table to the processor.

10. The system of claim 5, wherein the display device is a unified display that depicts various waveforms signals being collected as well as a pictogram indicating the computed likely position of the SCS stimulator electrode based on those inputs.

11. A method of optimally placing spinal cord stimulator (SCS) leads, comprising:
  acquiring components of somatosensory evoked potentials (SSEPs), compound action potentials and triggered EMG;
  analyzing waveforms; and
  quantifying waveform features in a single display such that a surgeon can quickly and easily determine optimal placement (as it relates to laterality and level of placement on the spinal cord) of SCS leads in a patient under general anesthesia without additional expert help.

12. The method of claim 11, further comprising:
  stimulating one or more peripheral nerves with one or more electrical pulses from one or more stimulating electrodes;
  recording resultant electrical waveforms generated by a nervous system of the patient in response to the electrical pulses using one or more recording electrodes; and
  identifying, with a computing device, the position of the spinal cord stimulator based on the resultant electrical waveforms or interference with the resultant electrical waveforms caused by activation of the SCS.

13. The method of claim 12, wherein the one or more stimulating electrodes may be coupled to one or more of an arm of the patient, a leg of the patient, an ulnar nerve of the patient, a median nerve of the patient, and a posterior tibial nerve of the patient.

14. The method of claim 12, wherein the one or more recording electrodes may be coupled to one or more of a head of the patient and a neck of the patient.

15. The method of claim 12, wherein the one or more recording electrodes may be coupled over muscles served by spinal nerves adjacent to the desired placement level of the SCS, including the 7th, 8th and 9th Thoracic levels and the 2nd to 8th Cervical levels.

16. The method of claim 12, wherein the resultant electrical waveforms are somatosensory evoked potential waveforms or compound motor action potentials or electromyographic potentials.

17. The method of claim 12, wherein the identifying includes one or more of:
  comparing, with the computing device, information based on the resultant electrical wave forms to information from an SCS machine to determine when changes in the resultant electrical waveforms are due to SCS stimulating activity; and
  comparing, with the one or more computing devices, information based on the resultant electrical waveforms to a baseline level of activity for each other to determine when changes in the resultant electrical waveforms are due to positioning of the SCS.

18. The method of claim 11, further comprising providing information based on the intensity of stimulation from an SCS.

19. The method of claim 11, further comprising alerting a user to the positioning of the SCS using one or more of a notification, an alert, a communication, an indication, and/or an alarm.

20. The method of claim 12, further comprising displaying information based on the resultant electrical waveforms on a display unit.

21. The method of claim 12, further comprising receiving a user input related to the accuracy of the resultant electrical waveforms.

22. The method of claim 12, further comprising activating, deactivating, or varying an intensity of the one or more stimulating electrodes of the SCS.

23. The method of claim 12, further comprising at least one of:
  identifying the position of the SCS electrode which may include one or more means for identifying changes in a latency of the resultant electrical waveforms;
  identifying changes in an amplitude of the resultant electrical waveforms; and
  identifying changes in a morphology of the resultant electrical waveforms.

\* \* \* \* \*